United States Patent
Abry et al.

(10) Patent No.: US 8,377,008 B2
(45) Date of Patent: Feb. 19, 2013

(54) DEVICE FOR THE AUTOMATIC INJECTION OF A PRODUCT IN AN INJECTION SITE

(75) Inventors: Herve Abry, Champagnier (FR); Lionel Maritan, Pierre Chatel (FR); Frederic Perot, St-paul De Varces (FR); Frank Carrel, Pont de Claix (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 96 days.

(21) Appl. No.: 12/681,650

(22) PCT Filed: Oct. 5, 2007

(86) PCT No.: PCT/FR2007/001634
§ 371 (c)(1),
(2), (4) Date: Jun. 25, 2010

(87) PCT Pub. No.: WO2009/043979
PCT Pub. Date: Apr. 9, 2009

(65) Prior Publication Data
US 2010/0262084 A1      Oct. 14, 2010

(51) Int. Cl.
*A51M 5/32* (2006.01)
(52) U.S. Cl. .................................. 604/198; 604/181
(58) Field of Classification Search ............ 604/181, 604/187, 192–198, 110
See application file for complete search history.

(56) References Cited

U.S. PATENT DOCUMENTS

| | | | |
|---|---|---|---|
| 6,979,316 B1 * | 12/2005 | Rubin et al. | 604/156 |
| 2005/0101919 A1 | 5/2005 | Brunnberg | |
| 2006/0229570 A1 | 10/2006 | Lovell et al. | |

FOREIGN PATENT DOCUMENTS

| | | |
|---|---|---|
| FR | 2 654 938 A1 | 5/1991 |
| FR | 2 899 482 A1 | 10/2007 |
| FR | 2 905 273 A1 | 3/2008 |
| WO | 02/47746 A1 | 6/2002 |
| WO | 2007/036676 A | 4/2007 |

* cited by examiner

*Primary Examiner* — Kevin C Sirmons
*Assistant Examiner* — Phillip Gray
(74) *Attorney, Agent, or Firm* — Hoffman & Baron, LLP

(57) ABSTRACT

According to the invention, first and second locking means (16, 12) are conformed to engage with each other and to permit the locking of an activation means (4) in at least one intermediate position between first and second positions of the activation means (4). The first and second locking means (12, 16) are conformed to be disengaged from each other when the protection member (3) is in a first position, in which a movement of a vessel contained in the device (1) is possible from an initial position to a position for inserting a needle contained in the vessel, and to be engaged with each other when the protection member (3) leaves said first position.

3 Claims, 1 Drawing Sheet

DEVICE FOR THE AUTOMATIC INJECTION OF A PRODUCT IN AN INJECTION SITE

Figure 1:
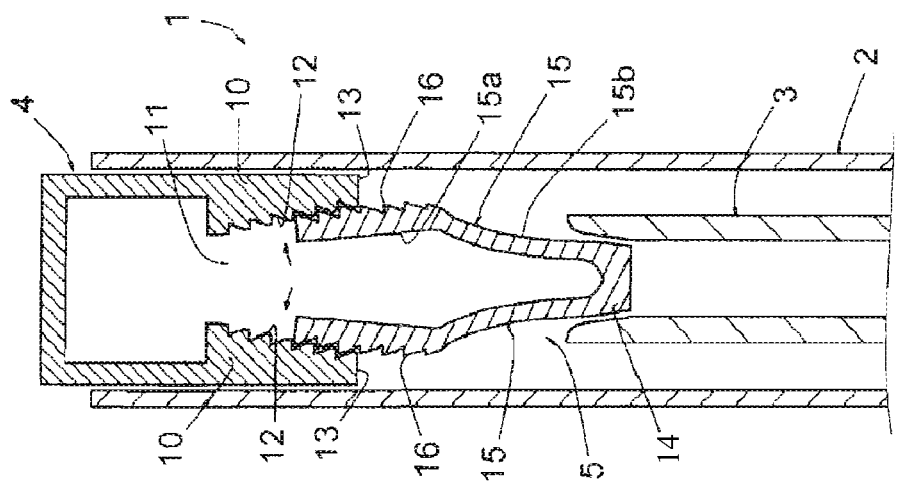

The present invention relates to a device for automatic injection of a product in an injection site.

In the following description, the terms "proximal" and "distal" should be considered in relation to the hand of the user having taken hold of the device, "proximal" relating to an area close to said hand and "distal" to an area away from the hand. Likewise, the term "distal direction" refers to the direction of the injection, and the term "proximal direction" designates the direction opposite the direction of injection.

An automatic injection device is a device allowing a user to inject a product himself. In an already-known manner, a device of this type comprises:
- a housing capable of receiving a container containing the product and provided with a needle, said container being movable relative to the housing between an initial position and an insertion position, distally spaced relative to the initial position;
- a safety shield connected to the housing and movable relative to said housing toward a first position in which a movement of the container from its initial position to its insertion position is possible and a second position, spaced in relation to the first position, the safety shield having a free end which is distally spaced beyond a distal end of the needle when the safety shield is in said second position;
- activating means, selectively movable from a first position to a second position in which the container is able to move from its initial position to its insertion position;
- first and second locking means for locking said activation means.

The assembly is such that, in said second position (second position) of the safety shield, said first and second locking means immobilize the activation means, thereby avoiding the risk of improper handling which may lead to a loss of product. The activating means are released when the safety shield has been sufficiently applied against the skin to be brought into said first position (first position).

In practice, the user holds the device by the housing and applies the safety shield against his skin such that said safety shield goes from the second position to the first position. This passage enables passage of the container, and therefore the needle, from the initial position to the insertion position, and makes it possible to free the movement of the activating means. The user then moves these activating means to perform the injection.

French patent application Nos. FR 06 07806 and FR 06 03200, in the applicant's name, illustrate known automatic injection devices.

The known devices make it possible to secure an automatic injection to a certain extent, but do not exclude all risks of improper handling. Indeed, users can be more or less stressed by the apprehension created by the injection and the pain they fear, and risk either more or less withdrawing the device after having begun to push on the activation means, such that the needle is not deep enough in the skin, or deciding to change the location of the injection at the last moment. This may result in defective actuation of the device, a wound from the injection needle and/or a more or less significant loss of product.

The main aim of the present invention is to resolve this drawback by providing an injection device having strengthened safety, strongly reducing the risk of improper handling during the injection.

Another aim of the invention is to provide a device maintaining a relatively simple structure and an acceptable production cost.

The concerned automatic injection device comprises, in a known manner:
- a housing capable of receiving a container containing the product and provided with a needle, this container being movable relative to the housing between an initial position and an insertion position, distally spaced in relation to the initial position;
- a safety shield coupled to and movable in relation to the housing to a first position in which movement of the container from its initial position to its insertion position is possible and a second position, spaced in relation to the first position, the safety shield having a free end which is spaced beyond a distal end of the needle when the safety shield is in said second position;
- activating means, selectively movable from a first position to a second position in which the container is able to move from its initial position to its insertion position;
- first and second locking means for locking said activating means.

According to the invention,
- the first and second locking means are formed to engage with each other and enable locking of the activating means in at least one intermediate position between said first and second positions of the activating means;
- the first and second locking means are formed to disengage from each other when the safety shield is in said first position and to engage with each other when the safety shield is out of said first position.

Thus, according to the invention, the device comprises locking means enabling locking of the activating means in at least one intermediate position, and which are brought to an unlocked position only when the safety shield is in said first position. Consequently, the loss of said first position will result in the locking means returning to mutual cooperation even if the activating means are in the aforementioned at least one intermediate position, this return leading to re-locking of the activating means.

This re-locking avoids the risks of improper handling related to losing the first position when the activating means have already been partially moved and are in said at least one intermediate position.

The device according to the invention therefore has greater safety with regard to defective handling.

The activating means may only control the injection; in this case, insertion of the needle into the patient's skin is done during the movement of the safety shield from said second position to said first position, this movement being such that the distal end of the safety shield comes, during this movement, to this side of the free end of the needle, thereby enabling penetration of said needle in the patient's skin.

The activation means can also control both the insertion of the needle into the patient's skin and the injection; in this case, in said first position, the distal end of the safety member is always located beyond the free end of the needle, and it is the actuation of the activating means that controls the penetration of the needle.

Advantageously, said first and second locking means are formed to allow the locking of the activating means in one of a plurality of successive intermediate positions between the first and second position of the activating means.

Re-locking of the activating means is thereby possible according to one of a plurality of intermediate positions.

Said first and second locking means can in particular comprise complementary locks arranged on said activating means and on an intermediate actuation member, the complementary locks being able to engage with each other.

According to one preferred embodiment of the invention, said intermediate actuation member includes a base intended to be deflectably engaged with the safety shield when the safety shield is in its first position.

Advantageously, the safety shield can be locked in said second position.

Preferably, said first and second locking means engage with each other and lock said activating means in an intermediate position between said first and second positions if the safety shield is moved out of its first position prior to a predetermined displacement of the activating means.

This predetermined displacement is preferably sufficient to cause the container to move to its said insertion position.

The invention will be well understood, and other characteristics and advantages thereof will appear, in reference to the appended diagrammatic drawing, illustrating, as a non-limiting example, one preferred embodiment of the automatic injection device it concerns.

Figure 2:
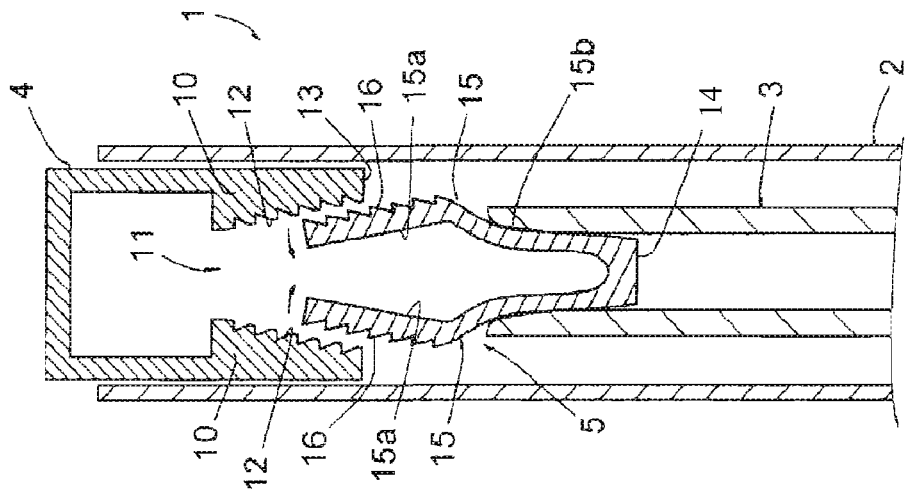
Figure 3:
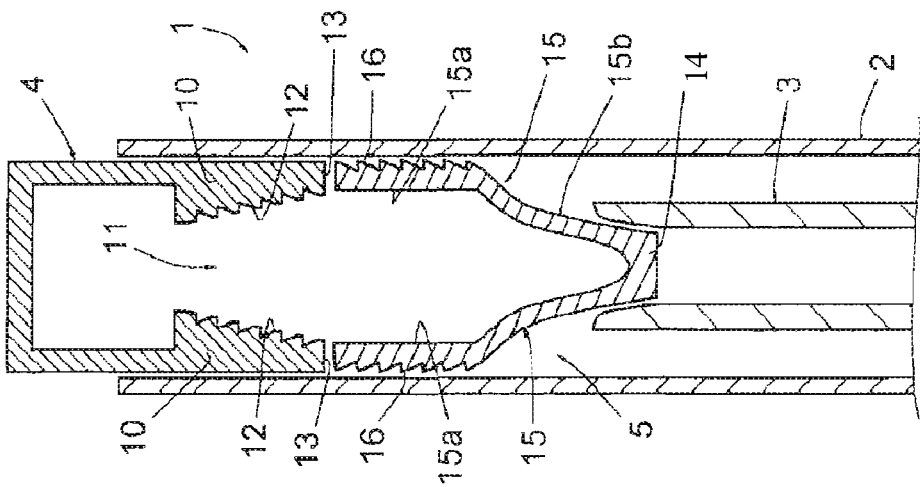

FIGS. 1 to 3 are greatly simplified diagrammatic views of said device, in cross-section through its longitudinal axis, during three positions of use, namely a resting position, an intermediate position allowing insertion of the needle and injection, and a re-locking position of a proximal actuation button it comprises in this intermediate position, respectively.

The figures illustrate an automatic injection device 1, comprising:
- a syringe body, a hollow injection needle and a piston engaged in the syringe body (not illustrated);
- a housing 2;
- a protecting tube 3;
- a spring (not shown) normally maintaining the protecting tube 3 in the resting position (called "second position") shown in FIG. 1;
- a proximal actuation button 4, making it possible to control the movement of the syringe body from an initial position to an insertion position of the needle and/or to control the injection, and
- an intermediate actuation member 5.

The housing 2 is intended to be seized by the user at the time of the injection.

The protecting tube 3 is engaged around the syringe body and the injection needle, and is engaged in the housing 2 while slidingly mobile relative to said housing. This mobility takes place between said second position (cf. FIG. 1), in which the distal end of the protecting tube 3 is located beyond, distally, the distal end of the injection needle, protecting the user from any risk of injury which may be caused by said needle, and a position of use, called "first position" (cf. FIG. 2), in which the distal end of the tube 3 is located on this side, distally, of the distal end of the injection needle. The device 1 comprises means limiting sliding of the tube 3 relative to the body 2, acting such that the removal of the tube relative to the distal end of the needle is such that this removal corresponds to the ideal penetration depth of the needle in the patient's skin.

The figures show that the protecting tube 3 has, at its proximal end, a portion having a slightly flared shape and a rounded inner proximal edge.

The activation button 4 comprises a part (not shown) enabling control of the movement of the syringe body from said initial position to said insertion position. From the distal side, it is divided into two diametrically opposed parts 10, the facing surfaces of which are tilted relative to the longitudinal axis of the device 1 and defining an empty space 11 between them. These tilted surfaces each have a series of locks 12.

Moreover, each part 10 ends with a flat surface 13 oriented perpendicularly to the longitudinal axis of the button 4.

The intermediate actuation member 5 is generally V- or Y-shaped, i.e. it comprises two diametrically opposed lateral branches 15 and a base part 14 intended to be engaged in the protecting tube 3.

Each of these lateral branches 15 comprises, on the side of the button 4, a rectilinear portion 15a, provided with locks 16 on its radially external surface, and, on the side of the tube 3, a rounded base portion 15b, being slightly flared in the proximal direction.

The two base portions 15b are continuously connected to base part 14, which is, in the second position, engaged in the proximal end of the protecting tube 3, as shown by FIG. 1.

This member 5 is assembled through molding of a synthetic material having a degree of elastic deformation. In the normal, non-deformed position, the part 5 is as shown in FIG. 1, with its lateral branches 15 separated from each other and the proximal ends of said branches 15 arriving across from the distal flat surfaces 12 of the button 4 and thereby locking the axial movement of the latter. The member 5 can be elastically deformed until the position shown in FIG. 2, in which the lateral branches 15 are brought together until they arrive beyond the distal flat surfaces 12. The button 4 can then be engaged on the proximal portions 15a of these lateral branches 15 thanks to the empty space 11 defined by the two portions 10, such that the movement of this button 4 is released, allowing, through pressure on the proximal surface of this button, insertion of the needle and/or injection.

It is shown in FIG. 2 that deformation of the part 5 results from the arrival of the protecting tube 3 in said first position, this tube 3 bearing against the rounded distal portions 15b of the branches 15, which thereby form ramps to control the movement bringing the end portions 15a closer together.

In the context of normal usage of the device 1, the button 4 can be pressed in the distal direction until its proximal surface shows on the surface with the proximal end of the housing 2.

However, if the protecting tube 3 was just moving out of said first position shown in FIG. 2, and therefore was brought by the aforementioned spring into said second position shown in FIG. 1, it is shown in FIG. 3 that the two branches 15 would immediately be brought into positions of mutual separation under the elastic return effect of the material forming the part 5. This separation leads, according to the axial position of the button 4, to at least two locks 16, or more than two locks 16, to engage with two locks 12, or more than two locks 12, of the button 4. The engagement of these locks 16, 12 makes it possible once again to axially immobilize the button 4, and therefore to prevent continuation of the injection when the protecting tube 3 has not returned to said first position.

It must be noted that the plurality of locks and the plurality of locks allows locking of the activation button 4 in a plurality of successive intermediate positions.

As appears from the preceding, the invention provides an automatic injection device having, relative to the similar devices of the prior art, the determining advantages of having strengthened safety, strongly reducing the risk of improper handling during injection, and maintaining a relatively simple structure and an acceptable production cost.

The invention was described above in reference to one embodiment provided purely as an example. It goes without saying that it is not limited to this embodiment, but that it extends to all embodiments covered by the appended claims.

The invention claimed is:

1. A device for automatic injection of a product into an injection site, the device comprising:
    a tubular housing having an open proximal end;

a tubular safety shield movable with respect to said housing;

a button slidably disposed within said proximal end of said housing, said button including legs extending distally into said housing, said legs being spaced apart with inwardly facing surfaces having a plurality of first locking members defined thereon; and, an actuation member disposed in said housing, said actuation member including a base with branches extending proximally therefrom, said branches each having a plurality of second locking members defined on outwardly facing surfaces thereof, said second locking members being formed to complementarily engage said first locking members, said branches being spaced apart such that said branches are selectively inwardly deflectable, wherein, in an initial state, said first locking members are axially spaced from said second locking members, wherein, in a post-use state, said first locking members are in at least partial face-to-face engagement with said second locking members, wherein, said branches being caused to be inwardly deflected between said initial state and said post-use state, and wherein, with sufficient proximal movement of said shield relative to said actuation member, said shield engaging said branches so as to cause said branches to inwardly deflect.

2. A device as in claim 1, wherein said inwardly facing surfaces of said legs of said button are tapered so as to converge in a proximal to distal direction.

3. A device as in claim 1, wherein said shield telescopes over a portion of said actuation member in moving proximally relative thereto.

* * * * *

UNITED STATES PATENT AND TRADEMARK OFFICE
CERTIFICATE OF CORRECTION

PATENT NO. : 8,377,008 B2
APPLICATION NO. : 12/681650
DATED : February 19, 2013
INVENTOR(S) : Abry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
First Day of September, 2015

Michelle K. Lee
*Director of the United States Patent and Trademark Office*